US006309650B1

(12) United States Patent
Kim et al.

(10) Patent No.: US 6,309,650 B1
(45) Date of Patent: Oct. 30, 2001

(54) ATTENUATED JAPANESE ENCEPHALITIS VIRUS ADAPTED TO VERO CELL AND A JAPANESE ENCEPHALITIS VACCINE

(75) Inventors: Hyun Su Kim; Wang Don Yoo; Soo Ok Kim, all of Seoul; Sung Hee Lee, Kyungkwido; Sang Bum Moon, Kyungkwido; Sun Pyo Hong, Kyungkwido; Yong Cheol Shin; Yong Ju Chung, both of Seoul, all of (KR); Kenneth H. Eckels, Washington, DC (US); Bruce Innis, Washington, DC (US); Joseph R. Puniak, Washington, DC (US); Leonard N. Binn, Washington, DC (US); Ashok K. Srivastava, Washington, DC (US); Doria R. Dubois, Washington, DC (US)

(73) Assignees: Cheil Jedang Corporation, Seoul (KR); The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/486,392

(22) PCT Filed: Aug. 25, 1998

(86) PCT No.: PCT/KR98/00259

§ 371 Date: Jun. 15, 2000

§ 102(e) Date: Jun. 15, 2000

(87) PCT Pub. No.: WO99/11762

PCT Pub. Date: Mar. 11, 1999

(30) Foreign Application Priority Data

Aug. 28, 1997 (KR) .................................................. 97 42001

Aug. 28, 1997 (KR) .................................................. 97 42002

(51) Int. Cl.[7] .................................................. A61K 39/12
(52) U.S. Cl. .................................. 424/218.1; 424/184.1; 435/235.1; 435/236; 435/237; 435/245
(58) Field of Search .............................. 424/184.1, 218.1; 435/5, 41, 173.3, 236, 245, 235.1, 237, 375

(56) References Cited

FOREIGN PATENT DOCUMENTS 0 562 136    9/1993   (EP) .

OTHER PUBLICATIONS

Huiying et al. 1995. The study of adaptation of Japanese encephalitis virus in Vero cells. Virologica Sinica. vol. 10. No. 4. See the abstract on p. 277.*
Barret. 1997. Japanese encephalitis and dengue vaccines. Biologicals. Mar.; vol. 25, No. 1, pp. 27–34.*
Patent Abstracts of Japan, vol. 14, No. 535, 1990, JP 2–223531, Nov. 26, 1990.
Patent Abstracts of Japan, vol. 13, No. 339, 1989, JP 1–117780, Jul. 31, 1989.

* cited by examiner

*Primary Examiner*—James Housel
*Assistant Examiner*—Shanon A. Foley
(74) *Attorney, Agent, or Firm*—Burns, Doane, Swecker & Mathis, L.L.P.; Elizabeth Arwine

(57) ABSTRACT

An attenuated Japanese encephalitis virus adapted to Vero cell by passages on Vero cell is disclosed. A Japanese encephalitis vaccine comprising said attenuated virus is also disclosed.

12 Claims, 4 Drawing Sheets

A

← E

← C
← M

B

← E

← C
← M

C

← E

ATTENUATED JAPANESE ENCEPHALITIS VIRUS ADAPTED TO VERO CELL AND A JAPANESE ENCEPHALITIS VACCINE

BACKGROUND OF THE INVENTION

1. Field of the Invention

The present invention relates to an attenuated Japanese encephalitis virus adapted to Vero cell by passages on Vero cell and a Japanese encephalitis vaccine comprising said attenuated virus.

2. Description of the Prior Art

Japanese encephalitis (JE) is a mosquito-borne arboviral disease of major or public health importance in Asia. More than 35,000 cases and 10,000 deaths are reported annually from that continent, but official reports undoubtedly underestimate the true number of cases (Okuno, T. *World Health Stat Q.* 3: 120–31,1978; Umenei, T. et al. *Bull World Health Org.* 63: 625–31, 1985). The illness may be manifested by a febrile headache syndrome, aseptic meningitis, or encephalitis and about half of the survivors tend to have permanent neurologic and psychiatric sequelae (Burke, D. S. et al. The Arbovirus: *Epidemiology and Ecology* 3:63–92, 1988; Monath, T. P. *Virology* 763–814, 1990).

JE virus is one of 66 Flaviviridae, enveloped, positive-sense, single stranded RNA viruses that largely are vector-borne (Chambers, T. J. et al. *Ann. Rev. Microbiol.* 44:649–88, 1990). Morphologically, flaviviruses are spherical, approximately 40 nm in diameter, are composed of a lipid bilayer surrounding a neucleocapsid containing 11-kb genome complexed with a capsid (C) protein (Rice, C. M. et al. *Science* 229:726–33, 1985). Surface projections on the membrane are composed of glycosylated envelope (E) and membrane (M) proteins. A pre-M glycoprotein, present in intracellular nascent virions, is cleaved to the M protein, found in mature extracellular virions. Important physiological activities are associated with the 53-kd E protein, including hemagglutination, viral neutralization, virion assembly, membrane fusion, and viral binding to cellular receptors (Koshini, E. et al. *Virol.* 188:714–20, 1992).

There are three JE vaccines for humans (Tsai, T. et al. *Vaccines* 671–713, 1993). Of the three, only inactivated JE vaccine produced in mouse brain is available internationally. One manufacturer, the Research Foundation for Microbial Diseases of Osaka University (Biken) produces most of the inactivated JE vaccine distributed internationally; that vaccine was licensed in 1992 in the USA where it is distributed by Connaught Laboratories, Inc., as JE-VAX™. Inactivated and live attenuated JE vaccine prepared in primary hamster kidney (PHK) cells are distributed solely in China.

Inactivated JE vaccine produced in mouse brains was licensed in Japan in 1954. Because it is produced by cerebral injection of infant mice, it is laborious to manufacture and concerns about the possibility of vaccine-related neurological side effect were raised. Though successive refinements in the manufacturing process have increased its purity and potency (Oya, A. *Vaccination Theory and Practice* 69–82, 1975; Oya, A. *Acta Pediatr Jpn.* 30:175–84, 1988; Takaku, K. Biken J. 11:25–39, 1968), a moderate frequency of local and mild systemic reactions have been reported until recently (Hoke, C. H. et al. *New Engl J Med.* 319:608–14, 1988; Poland, J. D. et al. *J Infect Dis.* 161:878–82, 1990; Sanchez, J. L. et al. *Lancet* 335:972–73, 1990). Local tenderness, redness, and/or swelling at the injection site occur in 20% of vaccines. Mild systemic symptoms, chiefly headache, low-grade fever, myalgias, malaise, and gastrointestinal symptoms, are reported by 10 to 30% of vaccines. An apparently new pattern of adverse reactions including urticaria, angioedema, respiratory distress, erythema multiforme, erythema nosodum and severe neurological disorders have been reported since 1989, principally among travellers vaccinated in Australia, Europe, and North America (Anderson, M. M. et al. *Lancet.* 337:1044, 1991; Ruff, T. A. et al. *Lancet* 228:881–2, 1991). In addition, in 1992 and 1995 Ohtaki reported seven children with acute disseminated encephalomyelitis (ADEM) with changes on magnetic resonance images (MRI) after JE vaccination (Ohtaki, E. et al. *Pediatr Neurol.* 8:137–9, 1992; Ohtaki, E. et al. *J Neurol Neurosurg Psychiatry* 59:316–7, 1995). Also of note is that vaccination with rabies vaccine containing animal brain tissue has caused severe neurological complications (Plotkin, S. A. et al. *Vaccines* 661–2, 1994). For these reasons, the WHO has designated JE vaccine development as a high priority.

More recently, inactivated and live attenuated JE vaccine of China have proven to be effective, eliciting high titers of virus-neutralizing antibody and conferring solid protection (Tsai, T. el al. *Vaccines* 671–713, 1993). However, PHK cells in which Chinese vaccine were prepared are not approved by the World Health Organization (WHO) for viral vaccine production or licensed for human use by the developed countries. The principal disadvantage in using primary hamster cells for the production of vaccines is the uncertainty with regard to the quality of vaccine. Even if specific pathogen free hamsters are used, animals can unexpectedly become infected, being problematic for vaccine production. Occasionally an infection of this type could be undetected for along time. With these criticisms, further controlled studies of the safety of the vaccine are required to allow confidence regarding its widespread use. Another disadvantage of the vaccine production from primary cells is the low rate of harvest of the virus and high cost without allowing mass production.

In view of the above, there is a need for new JE vaccine which is produced in standard cell lines such as Vero or human diploid cells that have been accepted as human vaccine substrates, with good cost effectiveness. Vero cells are transformed but non-tumorigenic cells derived from monkey kidney. The Vero cell line is more advantageous than any other standard cell line in that Vero cells are more readily adaptable to large scale cell culture and as a transformed cell has an infinite life time.

It has now been found that JE virus can be grown in Vero cell culture. Considerable efforts had been made in the field of JE vaccine to produce vaccine in standard cells which permit effecting cell cultures at a large volume. Nevertheless, virus characterization including genetic stability, yield and process necessary for vaccine commercialization through cultivation with Vero cells had never met the requirements of human vaccine. Owing to these facts and to the difficulties of transposing a knowledge acquired in other virus cultures to JE virus, the prior art had not achieved success in the development of JE virus vaccine which is genetically stable and has a high immunogenic character from continuous cell lines. Among all these researches, none had resulted up to the present time in a new vaccine production which satisfies the criteria mentioned in this background.

The present invention suggests a development and a propagation of JE virus in continuous cell line, Vero cells for vaccine production which overcome previous problems in JE virus produced in mouse brain or primary cell lines. The present invention also identifies methodology developed to cultivate the JE virus and a downstream process for vaccine production with cost-effectiveness.

In addition, the present invention identifies methodology which improves upon the previously commercialized JE vaccines in the following ways.

1. Safety: The invented virus did not acquire the virulence through the Vero cell cultivation, reducing the hazards of production and affording an additional level of safety to recipients beyond that furnished by stringent control over the virus-inactivation process. This advantage has never been provided by the previously commercialized JE vaccines.
2. Increased supply in safer production substrate: The JE vaccine of the present invention is produced in the absence of bovine serum, making high yields and inexpensive and scalable production which are not achieved in the previously commercialized JE vaccines.
3. Less reactogenicity: No gelatin stabilizer is incorporated into the JE vaccine of the present invention, reducing the risk of vaccine reactions like those seen with the existing vaccine (Saskaguchi M. et al. Vaccines 68–69, 1998). In addition, undesirable bovine-derived components, incorporated in the existing JE vaccines are effectively eliminated. Conclusively, this safety point of the present invention has never been provided by the previous JE vaccine.
4. Increased potency: The success of scalable production with Vero cells and the absence of supplements for production, as well as the effective purification, permits the first use of potent adjuvants in formulating the JE vaccine. Although the use of the adjuvants in the vaccine formulation has been applied in other vaccine, transposing this knowledge to the JE vaccine has been in difficulty since none of the existing JE vaccines assure it's safe production.

In conclusion, none had resulted up to the present time in a new vaccine which satisfies the aforementioned advantages in the commercialization of JE vaccine.

Therefore, an object of the present invention is to provide a safe and effective JE vaccine produced in standard cell substrate to increase its acceptability in many countries. A further object of the invention is to provide an effective process for producing a highly purified stable vaccine and formulating a vaccine which has a high immuniogenic character with a small antigen amount.

SUMMARY OF THE INVENTION

In one aspect, the present invention provides an attenuated Japanese encephalitis virus adapted to Vero cell by passages on Vero Cell. The attenuated Japanese encephalitis virus of the present invention, which is referred to as CJ50003 herein, was deposited at the permanent collection of the Korean Culture Center of Microorganisms, Seoul, Korea, on Apr. 20, 1998 under the Budapest Treaty of the international recognition of the deposit of microorganisms for the purpose of patent procedure, and a subculture thereof can be obtained from the repository under the accession number KCCM-10125.

In another aspect, the present invention provides a Japanese encephalitis vaccine comprising an attenuated Japanese encephalitis virus adapted to Vero cell by passages on Vero cell.

BRIEF DESCRIPTION OF THE DRAWINGS

These and other features, aspects, and advantages of the present invention will become better understood with regard to the following description, appended claims, and accompanying drawings as follows:

DETAILED DESCRIPTION OF THE INVENTION

Figure 1:
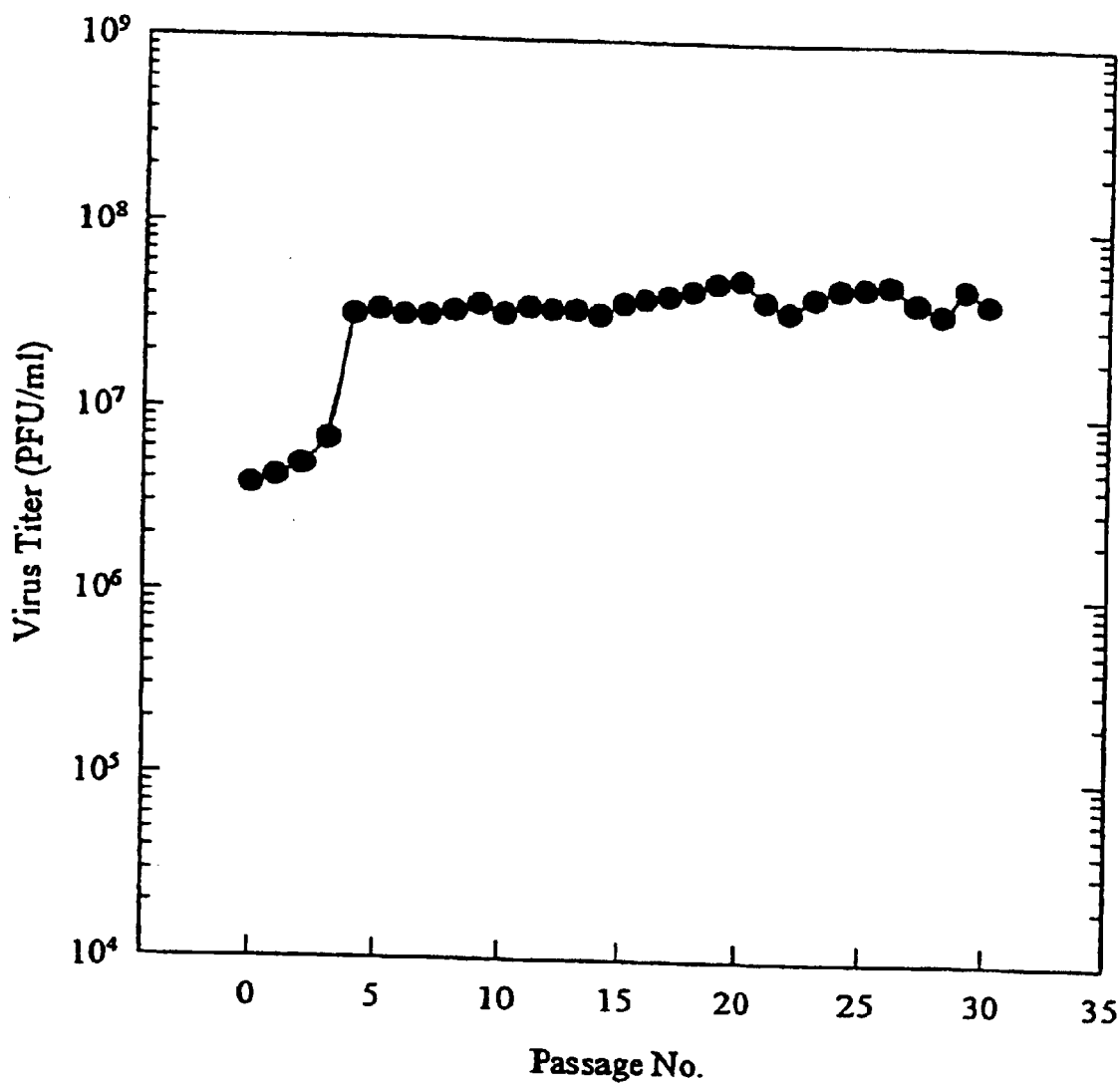
FIG. 1 shows passages and adaptation of JE virus SA14-14-2(PDK) in Vero cells. Virus passage 1 was harvested at 5 days after inoculation of Vero cell monolayer with 0.1 moi of SA14-14-2(PDK) strain. The JE virus titer was measured by plaque assay performed on Vero cell monolayers. Subsequent serial passages were conducted to 30 passages with virus passage 1 virus as starting material by successive virus infection and titration as described in Example 1.

The present invention relates to a JE virus strain which has desirable properties for the preparation of the JE vaccine. Said virus is an attenuated virus and can propagate in the continuous cell line, Vero which is admitted by WHO as cell substrate for human vaccine production. Thus it is expected that said virus can be used for the preparation of more safe inactivated and live JE vaccines than current vaccines.

The present invention provides a vaccine that satisfies the present need. A JE virus has been adapted to Vero cell by serial passages at no higher than 35° C. Continued passages in Vero cell resulted in increase in virus titer, over $10^7$ pfu per ml of culture supernatant and reduced culture time to show peak virus titer. The invention concerns the development of a multiple time harvesting process with no serum requirement as supplement resulted in high yield of virus productivity, which is commercially feasible properties for the large-scale production of said vaccine with cost-effectiveness. According to the invention, the multiple harvesting process in virus cultivation is responsible for the reduced degree of cytopathic effect (CPE) of infected cells. The JE vaccine of the present invention contains an extremely small quantity of residual cell derived components owing to the reduced level of CPE In addition, JE vaccine of the present invention is expected to afford enhanced immunogenicity and greater protection against disease than current JE vaccines. The purified JE vaccine of the present invention has a major advantage over current vaccines in that the purified viruses from the cultured Vero cells meet the development requirements for human vaccine.

The present invention also relates to the methods for the preparation of said vaccine. The methods can provide high productivity, purity and potency of said vaccine. The JE virus CJ50003 is obtained by subjecting JE virus SA14-14-2(PDK) to 4 passages or more of adapting in the Vero tissue culture cells at temperatures no higher than 35° C. and selecting the cultured virus while monitoring the virus propagation based on the number of foci which were formed in Vero and/or LLC-MK2 cells. The virus obtained from that adaptation has a peak titer of at least $1\times10^7$ pfu/ml of culture supernatant in Vero cell culture and reduced incubation period for harvest. The JE virus SA14-14-2 is an attenuated strain which is obtained by adapting a wild type JE virus SA14 from mosquito in the Primary Hamster Kidney (PHK) tissue culture cell and the Primary Dog Kidney (PDK) tissue culture cell (Kenneth H. Eckels, et al. *Vaccine* 6 513–518, 1988). But the PHK and PDK cells are not admitted by WHO, so they are not suitable for preparation of vaccines applicable to humans. The Vero cell is admitted by WHO for human use, so the Vero adapted JE virus strain, CJ50003, is a good basis for production of vaccine for humans.

It is known that SA14-14-2(PDK) virus belongs to flaviviridae and has the following physicochemical properties: single-stranded, positive-sense RNA genome with 5' methylated end and 3' end with no poly A structure. The size of RNA genome is approximately 11 kb and the genome is in a combined state with nucleocapsid (C) protein of 13,500 Da. The virus is additionally comprised of membrane (M) protein of 8,700 Da, envelope (E) protein of 53,000 Da and non-structural proteins NS1, 2a, 2b, 3, 4a, 5 and the like.

The Vero adapted JE virus strain, CJ50003 was passed in Vero cell over 30 passages. The virus titer and the morphology of plaque were not varied through passaging, suggesting that the virus has stable phenotypic character.

To get an insight into the molecular basis for the biological characteristics of JE virus CJ50003, the physicochemical properties of the virus were analyzed. The sequence of the bases of the viral genome was determined by cDNA cloning and sequencing. As a result, it was discovered that three adenine bases of the 1032, 1506, and 1704 positions, and a guanine base of the 1769 position of E protein gene of JE SA14-14-2(PDK) virus were replaced by three guanines and a thymine in JE CJ50003 virus, respectively. Accordingly, the amino acid sequence of E protein was changed from threonine of the 19 position, threonine of the 177 position, lysine of the 243 position and glutamine of the 264 position to alanine, alanine, glutamate and histidine, respectively. The amino acid changes on the E protein were maintained through passaging the virus in Vero cell as long as our investigation lasted.

The JE virus CJ50003 did not kill mice when the viruses which have different number of passages in Vero cells, were injected to young mice intracerebrally. Accordingly, it can be said that the Vero adapted JE virus CJ50003 is an attenuated and stable virus strain which has no or little neurovirulence. It is one of the critical points to use said virus for the live JE virus vaccine and/or inactivated vaccine.

The present invention also provides a method for purifying virus from cell culture without freezing the crude or interim purity materials. Said method comprises the steps of removing cell debris, concentrating the virus, purifying the virus by precipitation of the materials of cell origin and sucrose gradient ultracentrifugation, fractionating the gradients and assaying the fractions for virus. More specifically, the present invention provides a method for the production of purified JE virus, by propagating virus to high titer in continuous cell lines, in the presence or absence of serum protein supplements, purifying the virus by ultracentrifugation, and pooling the virus-positive fractions.

The said virus is propagated in Vero tissue culture cells. The confluently grown Vero cells in roller bottles are infected and incubated with the CJ50003 virus. Harvesting the virus can be done by the multiple harvesting method. The harvest of culture supernatant was started at the point of 2 or 3 days post infection according to moi of infection, and the fresh medium was refed to the culture. After 2 day incubation of the refed culture, the culture supernatant was harvested again. Harvesting can be repeated up to 4 times by 8 or 9 days post infection with the virus titer maintained over $10^7$ pfu/ml of culture supernatant. The multiple harvesting method gave a high yield of virus per unit roller bottle, so it makes this invention more compatible with the laws of market. Furthermore, the process is responsible for the reduced degree of CPE of infected cells. The reduced level of CPE contributes to extremely low level of residual cell derived components in JE vaccine of the present invention. The harvested culture supernatants can be stored at 4° C. until the purification started. The clarification of the harvested culture supernatants can be accomplished by common methods known in the art including low-speed centrifugation, for example, at 1500 g for 10 min, and/or by filtration through a filter of pore size of 0.45. The harvested culture fluid is stored at 4° C. until concentration. For the concentration of the virus, the culture fluid is ultrafiltrated and the retentate is collected. In another method for concentration, the polyethylene glycol (PEG) 8000 is dissolved in the culture fluid up to 10% and the precipitate is dissolved in a proper buffer, for example phosphate-buffered saline (PBS, pH 7.0). The protamine sulfate precipitation is performed for removing DNA or other materials which originated from the cell, which can be accomplished by addition of protamine sulfate to concentrated virus solution and high speed centrifugation, for example, at 12,000 g, for 5 min. For further purification of the virus, density gradient ultracentrifugation is performed on 15–60% continuous or multi-step sucrose gradients. The sucrose gradient is fractionated and the fractions are assayed for the virus. Methods for assaying for virus positive fractions include plaque assay, hemagglutination assay, polyacrylamide gel electrophoresis, and antigen assays such as immunoassays. The fractions for further processing are pooled on the basis of high virus titer and low level of other impurities. The purity of the pooled purified virus was estimated by testing for Vero cell originated chromosomal DNA and protein. The results showed that contents of host cellular DNA and protein are as low as 2.5 pg and 2 ng per 5 μg of purified JE virus, respectively, which demonstrated the purification methods described above effectively removed other impurities from viral antigen. JE virus yield from 1 L of infected culture fluid is estimated to be about 2.3 milligrams.

The present invention also provides a method of inactivating JE virus to destroy its infectivity while preserving its antigenicity. Said method comprises adding an effective quantity of formaldehyde and incubating said virus with said agent in certain conditions such that said virus is inactivated. Specifically, the fraction pool was diluted to appropriate protein concentration with a proper buffer such as PBS and the formaldehyde was added to the diluted fraction pool. The incubation with formaldehyde was performed at 22° C. or 4° C. At least 4 or 46 days were required to fully destroy viral infectivity without loss of viral antigenicity at 22° C. or 4° C, respectively. The inactivation process of JE virus at 22° C. was preferably chosen for simplicity in large scale culture and incubation time was extended to 7 days for a safety margin. However, examples of inactivating agents which were effective include but are not limited to formaldehyde. In general, this can be achieved by chemical or physical means. Chemical inactivation can be effected by treating the viruses, for example, with enzymes, β-propionlactone, ethylene-imine or a derivative thereof, and an organic solvent such as Tween, Triton, sodium deoxycholate, and sulphohetain. If necessary, the inactivating substance is neutralized afterwards; material inactivated with formaldehyde can, for example, be neutralized with thiosulphate. Physical inactivation can preferably be carried out by subjecting the viruses to energy-rich radiation, such as UV light, X-radiation or gamma-radiation.

The JE vaccines are prepared as injectables, either as liquid solution or suspension. It is possible to add a stabilizing agent such as carbohydrates (sorbitol, mannitol, starch, sucrose, dextran, glucose, etc), proteins (albumins, casein, etc) an agent containing proteins (bovine serum, skim milk, etc) and buffers (such as alkali metal phosphate). The preparation can be lyophilized after adding a stabilizer and it can be vacuum or nitrogen stored. If desired, one or more compounds with an adjuvant action can be added. Suitable compounds for this purpose are, for example, aluminum hydroxide, phosphate or oxide, mineral oil (such as Bayol, Marcol 52) and saponins. In addition, if desired, one or more emulsifiers, such as Tween and span, is also added to the virus materials.

The effectiveness of an adjuvant was determined by measuring the amount of neutralizing antibodies directed against the virus resulting from administration of the inactive virus in vaccines which are also absorbed to an adjuvant. Examples of adjuvant which was effective include but is not limited to alum hydroxide. The obtained vaccine was investigated for efficacy by the plaque reduction neutralization test (PRNT) with the sera of said vaccine immunized mice and direct challenge of immunized mice with a neurovirulent virus. As a result, it was shown that the said vaccine had the same as or better efficacy of eliciting neutralizing antibody than comparable vaccines.

To investigate possible changes in immunogenicity of Vero adapted viruses with different passage numbers, the vaccines were prepared in different passage numbers and the efficacy of each vaccine was compared. There was no remarkable difference in efficacy among the vaccines prepared from viruses with different passage numbers in spite of successive passing in Vero cell. Thus it can be said that the Vero adapted JE virus strain, CJ50003, has stable immunogenicity.

The following examples illustrate the attenuated JE virus adapted to Vero cell according to the present invention and the JE vaccine comprising said attenuated virus according to the present invention. From the foregoing description and the following examples, it is believed that those skilled in the art would be able to carry out the invention to the fullest extent.

EXAMPLE 1

Adaptation of SA14-14-2(PDK) Virus in Vero Cell

JESA14-14-2 (PDK), SA14-14-2 virus in dog kidney cell culture passage 8 was used to initiate serial passages in Vero cell culture. The Vero cell monolayers were inoculated with JE SA14-14-2 (PDK) at an moi of 0.1 pfu per cell. The infected cell cultures were grown in 25 cm$^2$ culture flasks containing 5 ml of nutrient media consisting of Eagle's minimal essential media supplemented with 10% fetal bovine serum in an atmosphere of about 5% $CO_2$ in air and at a temperature no higher than about 35° C., typically at from about 32° C. to about 35° C., with about 35° C. being preferred. Viral growth was monitored by microscopic observation of cytopathic effect (CPE) and various assay for the presence of viral antigen including hemadsorption assay (HA), plaque assay, and enzyme linked immunoadsorbant assay (ELISA). JE virus was harvested at day 5 post infection when the culture showed peak of virus titer, clarified by centrifugation. The single plaque was purified from the clarified supernatant and amplified in Vero cells. The amplified virus was re-infected to Vero cell for further passages. Subsequent serial passages were conducted up to 30 passages by successive virus infection, titration, and plaque-purification as described above. As shown in FIG. 1, the virus titers reached about 4×10$^7$ pfu per ml of culture supernatant with 4 passages in Vero cells and maintained close to this level in further passages. Besides, the optimal period for viral harvest was reduced from 5 days at passage 1 to 2–3 days at passage 4. A significant increase in virus yield, about 10$^5$ pfu/ml to over 10$^7$ pfu/ml and a decrease in incubation time resulted in the selection of the JE passage 4 in Vero cells as starting material of choice for the preparation of a candidate JE vaccine. The JE passage 4 in Vero cells was labelled as CJ50003 (Vero, PS4). Abbreviation PS means virus passage number in designated cell.

EXAMPLE 2

Characterization of CJ50003 Virus; Sequencing of the Envelope Gene and Neurovirulence Study As an effort to give an insight into the molecular basis for the biological characteristic of CJ50003 strain, the 1500 nucleotide sequence encoding the envelope(E) gene which possesses major neutralizing epitopes were determined and compared with those of the parent vaccine strains, SA14-4-2(PDK), SA14-14-2(PHK) and an wild type SA14 virus (Aihira, S. et al. *Virus Genes,* 5:95–109, 1991; Ni, H. et al. *J Gen Virol.* 76:401–407, 1995; Ni, H. et al. *J Gen Virol.* 76:409–413, 1995; Nitayaphan, S. et al. *Virology* 177:541–542, 1990). CJ50003 virus (Vero, PS4) was used for sequence analysis. This revealed that the C-tenninal region (amino acid 280–500) shows complete conservation, while the N-terminal region (amino acid 1–279) shows sequence variation among the virus strains. Mutations in the N-terminal region are almost evenly distributed. Nucleotide sequence of the E protein gene of CJ50003 differed from SA14/CDC by 8 nucleotides and 7 amino acids whereas SA14-14-2(PDK) differed from SA14/CDC by 7 nucleotides and 5 amino acids. The results were summarized in Table 1.

The sequence of CJ50003 virus differed from the published sequence of SA14-14-2(PDK) virus at 5 positions: nucleotide changes at positions 1032, 1506, 1704 and 1769 resulted in 4 amino acid differences between SA14-14-2 (PDK) and CJ50003 viruses: nucleotide changes at position 989 did not result in amino acid substitution. Higher passages of CJ50003 virus, i.e. passage 15 and 30 revealed no additional nucleotide changes. There were, therefore 5 distinct nucleotide and 4 amino acid changes between CJ50003 and parent virus, SA14-14-2(PDK) and these changes were stable on passage of this virus in cell culture. The Lys residue at 243 in the SA14-14-2(PDK), which is uniquely different compared with other attenuated JE viruses were substituted with Glu residue in CJ50003.

CJ50003 sequence also differed from the published sequence of SA14-14-2(PHK) virus (Aihira, S. et al. *Virus Genes*, 5:95–109, 1991). The nucleotide difference at 1032 caused amino acid difference at position E19 but the change at nucleotide position 989 did not result in amino acid substitution. Nucleotides at 1506 and 1704 in CJ50003 virus were the same as those present in the SA14-14-2(PHK) at these positions while different from the SA14-14-2(PDK) at those positions. The pattern of substitutions through the N-terminal region of the CJ50003 and SA14-14-2(PHK) E gene is almost same except for amino acid substitution at E19.

SA14-14-2(PHK), SA14-14-2(PDK) and CJ50003 viruses have 4 identical amino acid substitutions compared with the sequence of the parent SA14 virus at position E107, E138, E176 and E279. Of those the amino acids at position E138 and E176 (Ni, H. et al. *J Gen Virol.* 76:409–413, 1995), which were known to contribute to attenuation were still conserved after Vero adaptation, suggesting that CJ50003 did not lose it's attenuated character.

CJ50003 and the parent SA14-14-2(PDK) were tested for their mice neurovirulence by intracerebral (i.c.) injection into the 4-week-old BALB/c mice. The results are shown in Table 2. The lethality for young adult mice is not significantly different between SA14-14-2(PDK) and CJ50003 viruses which is very low compared to that of wild type SA14 virus. Thus it seems to be that the introduction to the Vero cell substrate did not provide a neurovirulent phenotype to the SA14-14-2(PDK) and CJ50003 virus still has attenuated character.

TABLE 2

Intracerebral virulence of 4-week-old mice inoculated with Vero-passaged CJ50003 viruses. PS represents passage in PDK or Vero cell.

| Virus | PFU Inoculum | log $LD_{50}$ ml$^{-1}$ | $LD_{50}$/PFU ratio |
|---|---|---|---|
| SA14 (PDK, PS3) | 2 × 10 (7) | 6.5 | 0.17[a] |
| SA14-14-2 (PDK, PS8) | 1.3 × 10 (6) | <1.5[b] | <0.00002[a] |
| CJ50003 (Vero, PS6) | 3.4 × 10 (7) | <1.5[b] | <0.000001 |
| CJ50003 (Vero, PS15) | 3.2 × 10 (7) | <1.5[b] | <0.000001 |
| CJ50003 (Vero, PS30) | 3.6 × 10 (7) | <1.5[b] | <0.000001 |

[a]Kenneth H. Eckels et al (Vaccine 6: 513–518, 1988).
[b]0/10 mice died after inoculation with undiluted virus.
The volume of inoculum for i.c. injection is 0.03 ml per mouse.

EXAMPLE 3

Virus Growth and Purification

Figure 2:
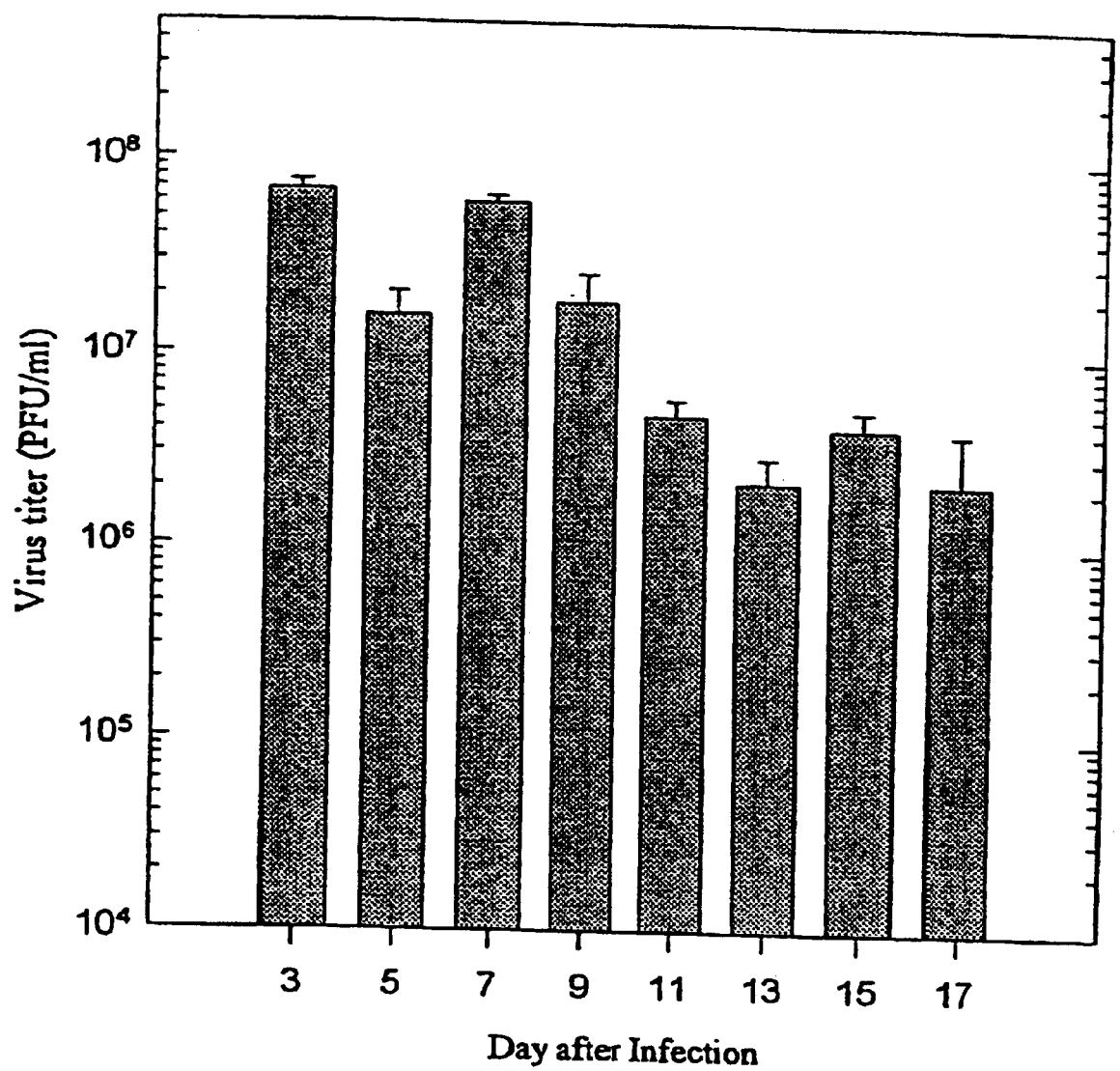
FIG. 2 shows multiple time harvest of JE virus CJ50003 in a roller bottle every other day from 3 to 17 days post infection. Vero cell monolayer were infected at a moi of 0.01 plaque forming unit (pfu) per cell. Virus was allowed to adsorb for 2 hrs at 35° C., then cells were washed with PBS three times, fed with 100 ml of serum-free EMEM and incubated at 35° C. Every 48 hrs from 3 days to 17 days post inoculation, culture supernatants were replaced with fresh serum-free EMEM. Virus infectivity titrations of the harvests were performed by plaquing on Vero-cell monolayers.

The production seed was prepared in virus passage 5 in Vero cell [CJ50003 (Vero, PS5)] and stored in deep-freezer. Vero cells were grown in Eagle's minimal essential medium (EMEM, Gibco) containing 10% fetal bovine serum (FBS, Gibco). Roller bottle cultures of Vero cell monolayers were infected with production seed virus at an moi of 0.01 to 0.1 pfu per cell. After 2 hours of virus adsorption, the cultures were washed 3 times with PBS and fed with EMEM not containing serum and incubated at 35° C. In infected Vero cell cultures, virus reached titers of around $10^7$ to $10^8$ pfu/ml at 2 or 3 days post infection. While virus harvests were taken 4 times at 2 day intervals until 8 or 9 days post infection starting from 2 or 3 days post infection, virus titers were still maintained over $10^7$ pfu/ml with very weak CPE. But after 9 days post infection, the titers were under $10^7$ pfu/ml (FIG. 2). The pooled harvests were centrifuged at 8,000 rpm for 15

TABLE 1

Comparison of nucleotide and amino acid sequences among JE virus strains, SA14, SA14-14-2 (PHK), SA14-14-2 (PDK), and CJ50003.

| Position | | Nucleotide | | | | | Amino Acid | | | | | |
|---|---|---|---|---|---|---|---|---|---|---|---|---|
| NT | AA | SA14/ USA | SA14/ CDC | SA14/J AP | SA14-14-2/PHK | SA14-14-2/PDK | CJ50003 | SA14/ USA | SA14/ CDC | SA14/J AP | SA14-14-2/PHK | SA14-14-2/PDK | CJ50003 |
| 989 | E4 | G | G | G | U | U | G | Leu | Leu | Leu | Leu | Leu | Leu |
| 1032 | E19 | A | A | A | A | A | G | Thr | Thr | Thr | Thr | Thr | Ala |
| 1052 | E25 | G | A | A | A | A | A | Leu | Leu | Leu | Leu | Leu | Leu |
| 1061 | E28 | U | U | U | C | C | C | Asp | Asp | Asp | Asp | Asp | Asp |
| 1217 | E80 | C | C | U | U | C | C | Ala | Ala | Ala | Ala | Ala | Ala |
| 1296 | E107 | C | C | C | U | U | U | Leu | Leu | Leu | Phe | Phe | Phe |
| 1389 | E138 | G | G | G | A | A | A | Glu | Glu | Glu | Lys | Lys | Lys |
| 1503 | E176 | A | A | A | G | G | G | Ile | Ile | Ile | Val | Val | Val |
| 1506 | E177 | A | A | A | G | A | G | Thr | Thr | Thr | Ala | Thr | Ala |
| 1704 | E243 | G | G | G | G | A | G | Glu | Glu | Glu | Glu | Lys | Glu |
| 1708 | E244 | G | A | A | A | A | A | Glu | Gly | Gly | Gly | Gly | Gly |
| 1769 | E264 | G | G | G | A | G | U | Gln | Gln | Gln | His | Gln | His |
| 1813 | E279 | A | A | A | U | U | U | Lys | Lys | Lys | Met | Met | Met |
| 1921 | E315 | C | U | C | U | U | U | Ala | Val | Ala | Val | Val | Val |
| 1977 | E334 | C | C | U | C | C | C | Pro | Pro | Ser | Pro | Pro | Pro |
| 2293 | E439 | A | G | A | G | G | G | Lys | Arg | Arg | Arg | Arg | Arg |
| 2441 | E488 | G | A | G | A | A | A | Gly | Gly | Gly | Gly | Gly | Gly |

Figure 3:
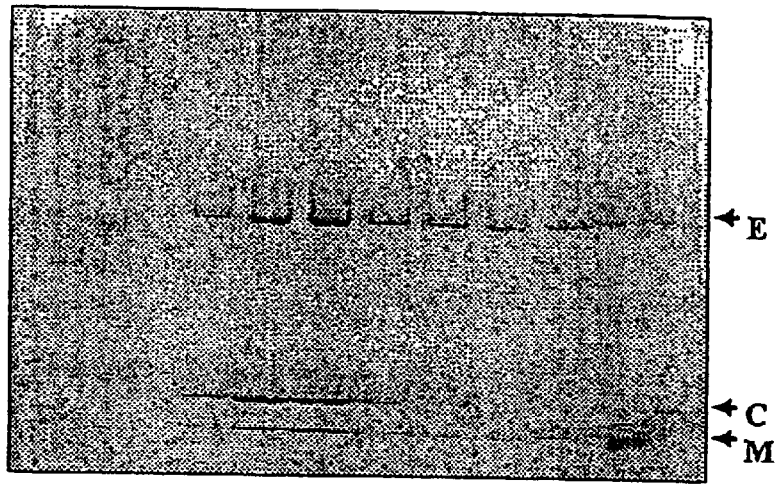
FIG. 3 shows an analysis of JE virus CJ50003 purified by sucrose gradient ultracentrifugation by SDS-PAGE and Western blotting. Sixty ml of concentrated culture supernatant was applied to a forty ml of 15–60% sucrose gradient and centrifuged in a 45 Ti rotor at 22,000 rpm, 18 hrs., 12° C. Two ml samples were collected from the bottom of the tube and subjected to 4–20% gradient SDS-PAGE and the resolved proteins were transferred to Nitrocellulose membranes. Proteins were visualized by staining with Coomassie brilliant blue (Panel A) or silver nitrate (Panel B), and antigens were visualized by reaction with monoclonal antibody reactive against JE viral E protein (Panel C). Lane 1, pre-stained protein standards (Novex Seeblue™) representing molecular weights of 250, 98, 64, 50, 36, 30, 16, and 6 kDa from the top; Lane 2–10, fraction No. 3–11 from the bottom after ultracentrifugation; E, envelope protein; C, capsid protein; M, membrane protein.
Figure 3:
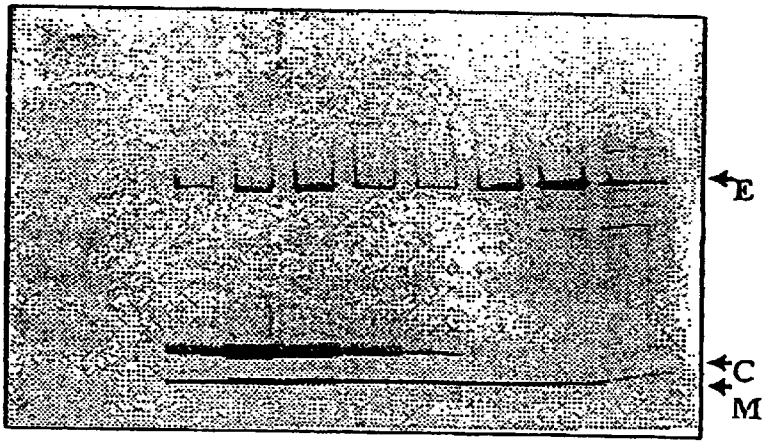
Figure 3:
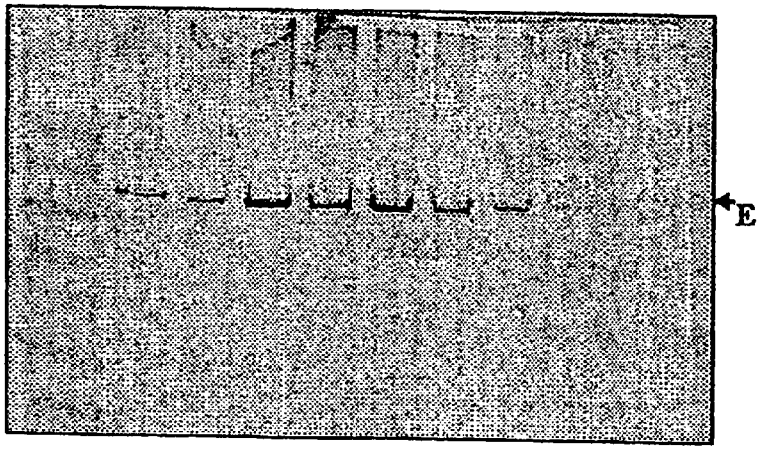

AA: amino acid;
NT: nucleotide position strains.

minutes and supernatants were filtered through a 0.45 $\mu$m filter. Virus culture supernatants were concentrated by ultrafiltration (Ultrasette, Filtron, 100k) or precipitation with PEG. The virus precipitated by PEG was collected by centrifugation and suspended in PBS or STE (10 mM Tris pH 7.2, 1 mM EDTA, 150 mM NaCl) buffer. Retentate after ultrafiltration was concentrated to 250 ml and the cassette was washed with 100 ml of PBS. Virus concentrates were chilled in the ice for 2 hours after adding 0.5–2 mg/ml of protamine sulfate and the supernatants obtained by centrifuging at 10,000 rpm for 5 minutes. The concentrated viruses were purified by ultra-centrifugation on sucrose gradients. The ultracentrifugation was carried out at 38,000 g for 18 hours. Fractions were subjected to electrophoresis on polyacrylamide gels containing the detergent sodium dodecyl sulfate (SDS-PAGE). The nucleocapsid protein (C, 13,500 Da), membrane protein (M, 8,700 Da) and envelope protein (E, 53,000 Da) bands were seen in the SDS-PAGE (FIG. 3, panel A). Envelope antigens (E) were detected by Western blotting with mouse anti-JE virus monoclonal antibody (FIG. 3, panel C). Virus positive fractions, fraction Nos.4 to 9, in which other protein bands except viral proteins were not apparent in silver stained gel (FIG. 3, panel B) were pooled, and assayed for protein concentration by Lowry method. Detailed results are shown from two purifications from infected Vero cultures either concentrated with tangential flow ultrafiltration or by PEG8000 precipitation (Tables 3 and 4). Purified virus was diluted with two volumes of PBS, added to the final 0.01% of Tween80, and filtered through a 0.22 $\mu$m filter.

TABLE 3

Purification of JE virus by concentration with tangential flow ultrafiltration.

| Sample | Total Volume (ml) | Total pfu | % Yield (mg) | Total protein tein) | % Yield (pro- mg) | Specific Activity (pfu/ |
|---|---|---|---|---|---|---|
| Pooled culture super-natant | 10,000 | $4.4 \times 10^{11}$ | 100 | 600 | 100 | $7.3 \times 10^{7}$ |
| Filtron concen-trate | 200 | $4.0 \times 10^{11}$ | 90 | 280 | 47 | $1.4 \times 10^{8}$ |
| Sucrose gradient pool | 500 | $3.8 \times 10^{11}$ | 86 | 42 | 7 | $9.0 \times 10^{9}$ |
| 0.22 $\mu$ filtration | 50 | $2.4 \times 10^{11}$ | 55 | 23 | 3.8 | $1.0 \times 10^{10}$ |

TABLE 4

Purification of JE virus by concentration with PEG8000 precipitation.

| Sample | Total Volume (ml) | Total pfu | % Yield (pfu) | Total protein (mg) | % Yield (pro- tein) | Specific Activity (psu/ (mg) |
|---|---|---|---|---|---|---|
| Pooled culture super-natant | 10,000 | $4.4 \times 10^{11}$ | 100 | 600 | 100 | $7.3 \times 10^{7}$ |
| PEC precipitate | 200 | $2.7 \times 10^{11}$ | 61 | 40 | 6.7 | $6.8 \times 10^{9}$ |
| Sucrose gradient pool | 500 | $2.5 \times 10^{11}$ | 56 | 15 | 2.5 | $1.7 \times 10^{10}$ |
| 0.22 $\mu$ filtration | 50 | $1.6 \times 10^{11}$ | 41 | 12 | 2 | $1.3 \times 10^{10}$ |

The virus preparations were compared for relative purity using specific activity measurements (i.e., pfu/mg protein). Virus purified from concentrate by ultrafiltration had about the same activity as virus purified from concentrate by PEG8000 precipitation. Also the purity of the pooled purified viruses was estimated by testing for Vero cell originated chromosomal DNA and protein. The results showed that contents of host cellular DNA and protein are as low as 2.5 pg and 2 ng per 5 $\mu$g of purified JE virus respectively regardless of method of concentration, which demonstrated that both purification methods described above effectively removed other impurities from viral antigen. However in terms of protein yield of purified virus, the purification method using ultrafiltration is 2-fold better than the purification method involving PEG8000 precipitation.

EXAMPLE 4

Virus Inactivation

Figure 4:
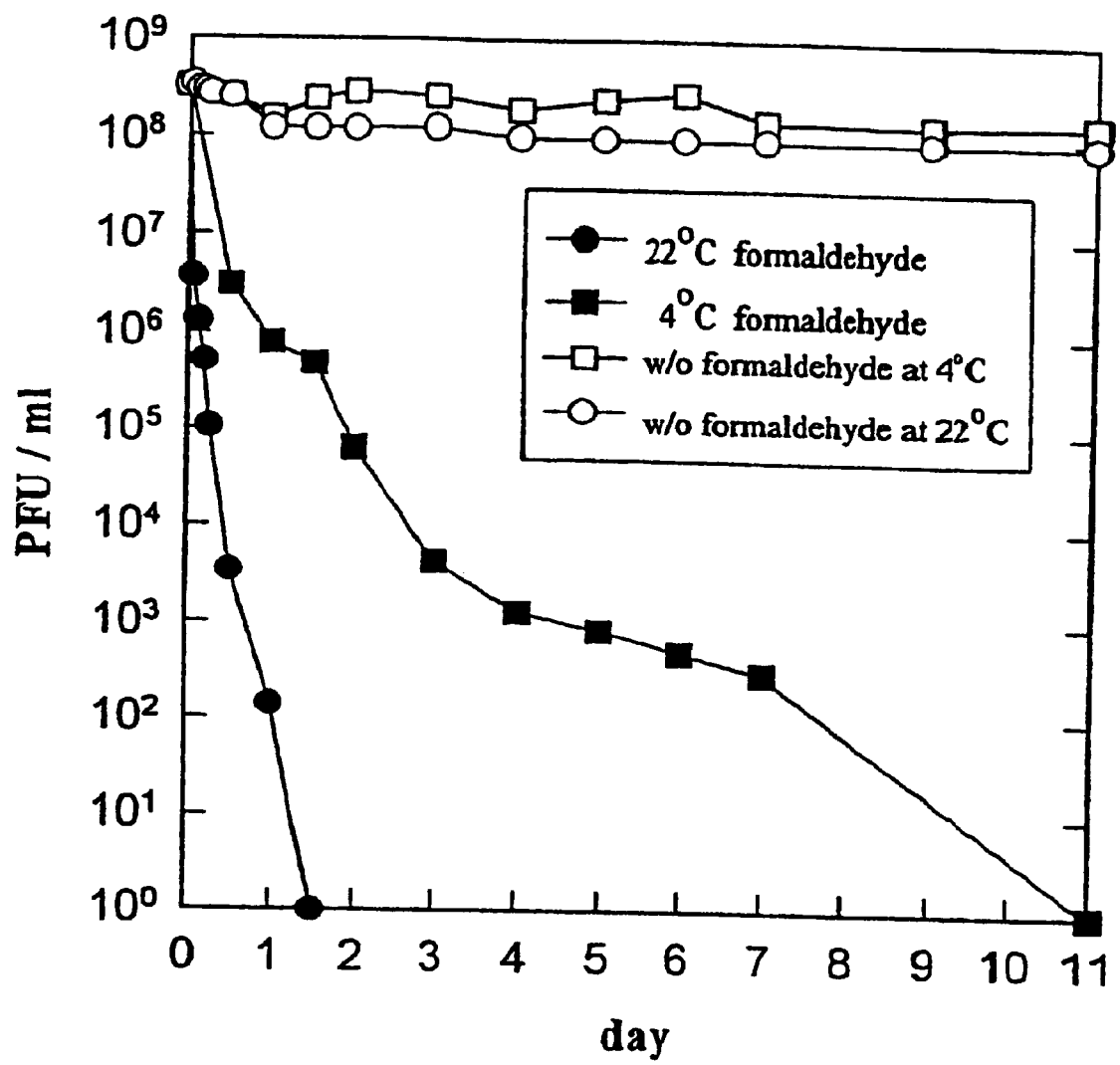
FIG. 4 shows formaldehyde inactivation kinetics of purified JE virus CJ50003. Purified JE virus preparations were inactivated with 0.018% formaldehyde at 4° C. or 22° C. Samples taken at the indicated times were titrated for their residual infectious virus by direct plaquing on Vero cell monolayers. Additionally, amplification assay was done to detect low levels of virus as follows. Duplicate flasks containing Vero cell monolayers were inoculated with samples from virus-inactivation time points. After a 2 hr adsorption period at 35° C., cells were refed and incubated at 35° C. Cells were refed at 7 days and at 14 days post-infection. The culture media were harvested and plaqued to detect infectious virus. Inactivation time points from two separate experiments are shown: 4° C. (filled rectangle), 22° C. (filled circle). Thermal inactivation (no formaldehyde) controls (open rectangle for 4° C. and open circle for 22° C.) were done in parallel.

Purified virus was either directly used for preparation of live attenuated vaccine after dialysis with PBS or inactivated with formaldehyde for preparation of inactivated vaccine. Inactivation with 0.018% formaldehyde was carried out at 22° C. or 4° C. Samples were taken at regular intervals and assayed directly for infectious virus by plaque titration (FIG. 4). Samples which were negative by direct plaque assay were subjected to blind passage on Vero cell monolayers in order to amplify low levels of virus and then re-plaqued. It was found that 4 days at 22° C. or 46 days at 4° C. were required for complete inactivation of infectivity (Tables 5 and 6). The antigenicity of the virus was monitored during inactivation by testing samples with the antigen spot blot assay and polyclonal antisera. By this assay there appeared to be no detectable losses in antigenicity after exposure to 0.018% formaldehyde for up to 10 days at 22° C. or 15 days at4° C.

Inactivation with formaldehyde under these conditions was carried out for at least 7 days at 22° C. or 60 days at 4° C., giving a margin of safety. After inactivation, free formaldehyde in the samples was neutralized by the addition of 0.038% of sodium metabisulfite. Dialysis was carried out concurrently with PBS and then filtered through a 0.22 $\mu$m filter.

TABLE 5

Formaldehyde inactivation of JE virus, CJ50003 at 4° C.

| Day | JE virus (−HCHO) | JE virus (+HCHO) | Amplification |
|---|---|---|---|
| 0 | $3.2 \times 10^{8}$ | $3.2 \times 10^{8}$ | + |
| 0.5 | $2.6 \times 10^{8}$ | $3.2 \times 10^{6}$ | + |
| 1 | $1.52 \times 10^{8}$ | $7.9 \times 10^{5}$ | + |
| 1.5 | $2.4 \times 10^{8}$ | $4.8 \times 10^{5}$ | + |
| 2 | $2.8 \times 10^{8}$ | $6.4 \times 10^{4}$ | + |
| 3 | $2.6 \times 10^{8}$ | $4.3 \times 10^{3}$ | + |
| 4 | $1.9 \times 10^{8}$ | 1300 | + |
| 5 | $2.4 \times 10^{8}$ | 285 | + |
| 6 | $2.8 \times 10^{8}$ | 480 | + |
| 7 | $1.5 \times 10^{8}$ | 200 | + |
| 11 | $1.5 \times 10^{8}$ | 0 | + |
| 22 | $1.4 \times 10^{8}$ | 0 | + |
| 32 | $1.2 \times 10^{8}$ | 0 | + |
| 46 | $1.0 \times 10^{8}$ | 0 | − |
| 60 | $1.0 \times 10^{8}$ | 0 | − |

TABLE 6

Formaldehyde inactivation of JE virus at 22° C.

| Hour | JE virus (-HCHO) | JE virus (+HCHO) | Amplification |
|---|---|---|---|
| 0 | $3.2 \times 10^8$ | $3.2 \times 10^8$ | + |
| 3 | $3.0 \times 10^8$ | $1.3 \times 10^6$ | + |
| 6 | $2.7 \times 10^8$ | $1.1 \times 10^5$ | + |
| 12 | $2.5 \times 10^8$ | $3.5 \times 10^5$ | + |
| 24 | $1.2 \times 10^8$ | 140 | + |
| 36 | $1.2 \times 10^8$ | 0 | + |
| 48 | $1.2 \times 10^8$ | 0 | + |
| 72 | $1.1 \times 10^8$ | 0 | + |
| 96 | $1.1 \times 10^8$ | 0 | − |
| 360 | $1.0 \times 10^8$ | 0 | − |

EXAMPLE 5

Immunogenicity of CJ50003 Purified, Inactivated Virus (PIV) and Live Attenuated Virus (LAV) in Mice The immunogenicities of LAV and PIV were then tested in mice with previously commercialized Biken inactivated vaccine. Groups of 20 six-week-old BALB/c mice were immunized intraperitoneally (i.p.) with three kinds of immunogen. Immunization was done with two inoculations without an adjuvant at intervals of 2 weeks. Two weeks post second immunization sera were obtained from each group of mice, pooled and subsequently tested for the presence of neutralizing antibodies by PRNT method (Table 7). As shown in Table 7, there was no significant difference in neutralizing antibody titer between groups which received three kinds of immunogen.

TABLE 7

Induction of neutralizing antibodies in mice immunized with PIV or LAV

| Immunogen | Dose | Titers of neutralizing antibodies[a] |
|---|---|---|
| PIV | 5 µg | 1:320 |
| PIV | 10 µg | 1:320 |
| LAV | 5 µg | 1:320 |
| LAV | 10 µg | 1:640 |
| Biken vaccine[b] | 1 dose | 1:320 |

[a]Titer of neutralizing antibody is defined as the reciprocal of serum dilution resulting in 50% reduction of mouse brain passaged Nakayama virus plaques.
[b]Biken vaccine 1 dose contains 5 µg of viral protein (TCA-precipitable) according to the manufacturer.

The Immunogenicity of PIV was further tested in mice. Adult, in bred mice were immunized with various dilutions of inactivated virus with or without an alum adjuvant. Groups of 20 six-week-old BALB/c mice were immunized subcutaneously with 500, 50, and 5 ng of PIV either in saline or saline with aluminum hydroxide (Rehydragel). Mice received two inoculations spaced 3 weeks apart. Sera were pooled from each group of mice at 3 weeks post second immunization, and tested for the presence of neutralizing antibodies with mouse brain passaged Nakayana strain as neutralized virus (Table 8). PIV was better than Biken vaccine in all doses and adjuvant significantly improved the immune response of mice to 50 and 500 ng of PIV about 4 and 8 fold, respectively.

TABLE 8

Comparison of the titer of neutralizing antibody in mice immunized with PIV with or without alum hydroxide.

| Immunogen | Dose | Titers of neutralizing antibodies[a] |
|---|---|---|
| PIV | 500 ng | 1:160 |
| PIV | 50 ng | 1:40 |
| PIV | 5 ng | 1:20 |
| PIV + alum | 500 ng | 1:1280 |
| PIV + alum | 50 ng | 1:160 |
| PIV + alum | 5 ng | 1:20 |
| Biken vaccine | 1/10 dose | 1:80 |
| Biken vaccine | 1/100 dose | 1:10 |
| Biken vaccine | 1/1000 dose | 1:10 |

[a]Titer of neutralizing antibody is defined as the reciprocal of serum dilution resulting in 50% reduction of mouse brain passaged Nakayama virus plaques.
[b]Biken vaccine 1 dose contains 5 µg of viral protein (TCA-precipitable) according to the manufacturer.

The in vivo protective efficacy of PIV was then tested in BALB/c mice. For protection assays, groups of 10 three-week-old BALB/c mice were inoculated subcutaneously in the hindquarters with inactivated JE viruses in saline or saline with aluminum hydroxide (Rehydragel). Age-matched controls were inoculated with PBS or non-specific antigens in alum. Mice were boosted with an equivalent dose three weeks later. The mice were challenged at 3 weeks post immunization by intracranial inoculation with 500 pfu of the mouse neurovirulent JE virus (Nakayama, mouse brain adapted) contained in 30 µl of PBS. Challenged mice were monitored daily for morbidity and mortality for up to twenty-one days. As shown in Table 9, mice immunized with 50 ng of PIV showed 90% of protection. Furthermore, mice immunized with 50 and 5 ng of PIV mixed with alum showed 100% and 70% protection, respectively while 1/100 dose of Biken vaccine protected just 50% of immunized mice. In comparison, all mice in the control group became sick and died beginning at five to seven days post-challenge.

TABLE 9

Protection of vaccinated mice against challenge with Nakayama virus[a] Immunogen

| Immunogen | Dose | Survivors |
|---|---|---|
| Control[b] | N/A | 0/10 |
| PIV | 500 ng | 10/10 |
| PIV | 50 ng | 9/10 |
| PIV | 5 ng | 3/10 |
| PIV + alum | 500 ng | 10/10 |
| PIV + alum | 50 ng | 10/10 |
| PIV + alum | 5 ng | 7/10 |
| Biken vaccine[c] | 1/10 dose | 10/10 |
| Biken vaccine | 1/100 dose | 5/10 |
| Biken vaccine | 1/1000 dose | 3/10 |

[a]Mice immunized with 2 inoculations of test vaccines spaced 3 weeks apart, then challenged with 500 pfu of mouse-neurovirulent Nakayama virus.
[b]Age-matched controls were inoculated with PBS or non-specific antigens in alum
[c]Biken vaccine 1 dose contains 5 µg of viral protein (TCA-precipitable) according to the manufacturer.

To investigate immunologic stability of CJ50003 virus over Vero cell passages, viruses with various passage numbers in Vero cell were independently purified and the immunogenicities were evaluated by the method as described in Table 8. As shown in Table 10, there was no remarkable difference in the ability to elicit neutralizing antibodies among vaccines prepared from the viruses with different virus passage numbers in Vero cell, indicating that CJ50003 virus is very stable over Vero cell passages in terms of immunogenicity.

TABLE 10

Vaccine potencies prepared with JE viruses with different virus passage numbers in Vero cells

| Immunogen[a] | Dose | Titers of neutralizing antibodies[b] | S.d.[c] |
|---|---|---|---|
| PIV-4ps | 0.5 μg | 1:150 | 20 |
| PIV-6ps | 0.5 μg | 1:145 | 15 |
| PIV-15ps | 0.5 μg | 1:130 | 28 |
| PIV-20ps | 0.5 μg | 1:140 | 18 |
| PIV-30ps | 0.5 μg | 1:160 | 13 |

[a]Immunogen (PIV-Xps); purified inactivated vaccine prepared with CJ50003 virus of which passage number in Vero cells is X.
[b]Titer of neutralizing antibody is defined as the reciprocal of serum dilution resulting in 50% reduction of mouse brain passaged Nakayama virus plaques and mean values of results from three separate experiments ere taken. 50% endpoint is determined by Reed and Muench method.
[c]Standard deviation The results presented here suggest that both an inactivated JE virus vaccine and live attenuated vaccine using CJ50003 strain show promise. Relatively fast and efficient processes were developed for growing JE virus in Vero cell, concentrating and purifying them to a degree which may be suitable for human use and inactivating them without measurable loss in antigenicity. These preparations were found to be immunogenic and protective in mice.

What is claimed is:

1. An attenuated Japanese encephalitis virus adapted to Vero cell by passages on Vero cell wherein said virus has a multiplicity of more than 1×10(7) PFU/ml in Vero cells and $LD_{50}$/pfu for young adult mouse is less than 0.000001.

2. A Japanese encephalitis vaccine comprising the attenuated Japanese encephalitis virus according to claim 1.

3. The vaccine according to claim 2, which further comprises pharmaceutically acceptable additives.

4. The vaccine according to claim 2 wherein the virus is inactivated by an inactivating. agent.

5. The vaccine according to claim 4, which further comprises pharmaceutically acceptable additives.

6. The vaccine according to claim 2 wherein the virus is live-attenuated JE virus untreated by an inactivating agent.

7. The vaccine according to claim 6, which further comprises pharmaceutically acceptable additives.

8. An attenuated Japanese encephalitis virus adapted to Vero cell by passages on Vero cell which is CJ50003.

9. A Japanese encephalitis vaccine comprising the attenuated Japanese encephalitis virus according to claim 8.

10. The vaccine according to claim 8, wherein the virus is inactivated by an inactivating agent.

11. The vaccine according to claim 8, wherein the virus is live-attenuated JE virus untreated by an inactivating agent.

12. The vaccine according to claim 9, which further comprises pharmaceutically acceptable additives.

* * * * *

UNITED STATES PATENT AND TRADEMARK OFFICE
CERTIFICATE OF CORRECTION

PATENT NO. : 6,309,650 B1
DATED : October 30, 2001
INVENTOR(S) : Kim, Hyun Su et al.

It is certified that error appears in the above-identified patent and that said Letters Patent is hereby corrected as shown below:

<u>Title Page,</u>
Item [75], please correct the name of the inventor(s) from:
"Hyun Su Kim; Wang Don Yoo; Soo Ok Kim; Sung Hee Lee; Sang Bum Moon; Sun Pyo Hong; Yong Cheol Shin; Yong Ju Chung; Kenneth H. Eckels; Bruce Innis; Joseph R. Puniak; Leonard N. Binn; Ashok K. Srivastava; Doria R. Dubois"
to read -- Hyun Su Kim; Wang Don Yoo; Soo Ok Kim; Sung Hee Lee; Sang Bum Moon; Sun Pyo Hong; Yong Cheol Shin; Yong Ju Chung; Kenneth H. Eckels; Bruce Innis; Joseph R. Putnak; Leonard N. Binn; Ashok K. Srivastava; Doria R. Dubois --

Signed and Sealed this

Tenth Day of February, 2004

JON W. DUDAS
*Acting Director of the United States Patent and Trademark Office*